(12) United States Patent
Wang et al.

(10) Patent No.: US 8,194,244 B2
(45) Date of Patent: Jun. 5, 2012

(54) SOLUTION SAMPLE PLATE WITH WELLS DESIGNED FOR IMPROVED RAMAN SCATTERING SIGNAL DETECTION EFFICIENCY

(75) Inventors: Liming Wang, Sunnyvale, CA (US); Grace Credo, San Mateo, CA (US)

(73) Assignee: Intel Corporation, Santa Clara, CA (US)

( * ) Notice: Subject to any disclaimer, the term of this patent is extended or adjusted under 35 U.S.C. 154(b) by 372 days.

(21) Appl. No.: 11/770,945

(22) Filed: Jun. 29, 2007

(65) Prior Publication Data

US 2009/0002700 A1 Jan. 1, 2009

(51) Int. Cl.
*G01J 3/44* (2006.01)

(52) U.S. Cl. .................................................. 356/301

(58) Field of Classification Search .............. 356/300, 356/301, 244

See application file for complete search history.

(56) References Cited

U.S. PATENT DOCUMENTS

| | | | |
|---|---|---|---|
| 5,638,172 A * | 6/1997 | Alsmeyer et al. | 356/301 |
| 6,396,580 B1 * | 5/2002 | Tewes et al. | 356/246 |
| 7,255,474 B2 * | 8/2007 | Cong et al. | 374/131 |

* cited by examiner

*Primary Examiner* — Tarifur Chowdhury
*Assistant Examiner* — Abdullahi Nur
(74) *Attorney, Agent, or Firm* — Pillsbury Winthrop Shaw Pittman LLP (57) ABSTRACT

Devices, methods of using the device, systems including the device that include a sample plate with sample containers (wells), wherein at least a portion of the surface of the sample plate and/or sample containers is coated with an optical reflective material. The optical reflective material, provides enhanced excitation signal intensity and enhanced Raman signal intensity. Such enhancement provides improved total signal detection capabilities, and methods of improved focusing algorithms.

36 Claims, 3 Drawing Sheets

$$\text{Volume of Sample in semi-spherical well} = \frac{1}{2}\left(\frac{4}{3}\pi r^3\right) + \Delta \pi r^2 = V$$

Figure 1

Volume of Sample in semi-spherical well = $\frac{1}{2}\left(\frac{4}{3}\pi r^3\right) + \Delta \pi r^2 = V$

SOLUTION SAMPLE PLATE WITH WELLS DESIGNED FOR IMPROVED RAMAN SCATTERING SIGNAL DETECTION EFFICIENCY

FIELD OF INVENTION

Embodiments of the invention relate to sample plates with one or more containers for holding fluidic samples, wherein the sample plate containers are designed to improve Raman scattering signal detection efficiency.

BACKGROUND

The ability to detect, identify, and quantify trace quantities of analytes has become increasingly important in virtually every scientific discipline, ranging from part per billion analyses of pollutants in sub-surface water to analysis of cancer treatment drugs in blood serum. Raman spectroscopy is one analytical technique that provides rich optical-spectral information, and surface-enhanced Raman spectroscopy (SERS) has proven to be one of the most sensitive methods for performing quantitative and qualitative analyses. A Raman spectrum, similar to an infrared spectrum, consists of a wavelength distribution of bands corresponding to molecular vibrations specific to the sample being analyzed (the analyte). In the practice of Raman spectroscopy, the beam from a light source, generally a laser, is focused upon (impinged upon) a sample (solid or solution) to thereby generate inelastically scattered radiation, which is then optically collected and directed into a wavelength-dispersive spectrometer in which a detector converts the energy of impinging photons to electrical signal intensity.

Among many analytical techniques that can be used for chemical structure analysis, Raman spectroscopy is attractive because of its capability to provide rich structure information from a small optically-focused area or detection cavity, such as one or more a small sample containers ("wells") located in a sample plate. Compared to a fluorescent spectrum that normally has a single peak with half peak width of tens of nanometers to hundreds of nanometers, a Raman spectrum has multiple bonding-structure-related peaks with half peak width of as small as a few nanometers.

Currently, most commercial Raman instruments are designed to analyze solid samples. High-throughput type instruments (i.e., multiple samples per run) use non-confocal excitation/detection, while samples requiring higher laser excitation and analyte detection sensitivity usually are analyzed in a single sample per run. Confocal based Raman instruments, compared to non-confocal, are difficult to automate due to inconsistencies in automated focusing. Also, Raman signals are generated by measuring light reflectivity from the samples. Because a certain amount of laser light is lost due to scattering and other causes, useful signal intensity is lost.

With surface-enhanced Raman scattering detection (SERS), sensitivity of detection is much improved due to the chemical and electronic effects of high surface area materials interacting with analyte but, still, current commercial products and systems are not yet optimized for SERS analysis.

In solution-based samples of SERS active particles or standard Raman samples, a reflective sample container (well) would increase the laser excitation signal intensity impinging on the sample, and an engineered reflective surface could better direct the resulting Raman signal intensity into the collection optics and the path of the detection for improved signal intensity.

DETAILED DESCRIPTION

Embodiments of the invention relate to sample plates with one or more containers for holding fluidic samples, wherein the sample plate containers (wells) are surface coated to improve Raman scattering signal detection efficiency. Embodiments also include methods of using surface-enhanced sample containers to improve signal detection efficiency, and methods for improving focusing algorithms to detect excitation signal emanating from sample containers. Embodiments also relate to systems for quantifying the amount of an analyte in a mixture using Raman spectroscopy and optically-reflective enhanced sample plates/containers. The invention transcends several scientific disciplines such as polymer chemistry, biochemistry, molecular biology, medicine and medical diagnostics.

As used in the specification and claims, the singular forms "a," "an," and "the" include plural references unless the context clearly dictates otherwise. For example, the term "an array" may include a plurality of arrays unless the context clearly dictates otherwise.

An "array," "macroarray," or "microarray" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the sample spots on the array. A macroarray generally contains sample spot sizes of about 300 microns or larger and can be easily imaged by gel and blot scanners. A microarray would generally contain spot sizes of less than 300 microns. A multiple-well array is a support that includes multiple chambers for containing sample spots.

"Solid support," "support," and "substrate" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations.

The term "analyte," "target," or "target molecule" refers to a molecule of interest that is to be analyzed. The analyte may be a Raman active compound or a Raman inactive compound. Further, the analyte could be an organic or inorganic molecule. Some examples of analytes may include a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires, nanoclusters or nanoparticles. The analyte molecule may be fluorescently labeled DNA or RNA.

The term "probe" or "probe molecule" refers to a molecule that binds to a target molecule for the analysis of the target. The probe or probe molecule is generally, but not necessarily, has a known molecular structure or sequence. The probe or probe molecule is generally, but not necessarily, attached to the substrate of the array. The probe or probe molecule is typically a nucleotide, an oligonucleotide, or a protein, including, for example, cDNA or pre-synthesized polynucleotide deposited on the array. Probes molecules are biomolecules capable of undergoing binding or molecular recognition events with target molecules. (In some references, the terms "target" and "probe" are defined opposite to the definitions provided here.) The polynucleotide probes require only the sequence information of genes, and thereby can exploit the genome sequences of an organism. In cDNA arrays, there could be cross-hybridization due to sequence homologies among members of a gene family. Polynucleotide arrays can be specifically designed to differentiate between highly homologous members of a gene family as well as spliced forms of the same gene (exon-specific). Polynucleotide arrays of the embodiment of this invention could also be designed to allow detection of mutations and single nucleotide polymorphism. A probe or probe molecule can be a capture molecule.

The terms "die," "polymer array chip," "DNA array," "array chip," "DNA array chip," or "bio-chip" are used interchangeably and refer to a collection of a large number of probes arranged on a shared substrate which could be, for example, a portion of a silicon wafer, a nylon strip or a glass slide.

The term "chip" or "microchip" refers to a microelectronic device made of semiconductor material and having one or more integrated circuits or one or more devices. A "chip" or "microchip" is typically a section of a wafer and made by slicing the wafer. A "chip" or "microchip" may comprise many miniature transistors and other electronic components on a single thin rectangle of silicon, sapphire, germanium, silicon nitride, silicon germanium, or of any other semiconductor material. A microchip can contain dozens, hundreds, or millions of electronic components.

The term "molecule" generally refers to a macromolecule or polymer as described herein. However, arrays comprising single molecules, as opposed to macromolecules or polymers, are also within the scope of the embodiments of the invention.

"Micro-Electro-Mechanical Systems (MEMS)" is the integration of mechanical elements, sensors, actuators, and electronics on a common silicon substrate through microfabrication technology. While the electronics are fabricated using integrated circuit (IC) process sequences (e.g., CMOS, Bipolar, or BICMOS processes), the micromechanical components could be fabricated using compatible "micromachining" processes that selectively etch away parts of the silicon wafer or add new structural layers to form the mechanical and electromechanical devices. Microelectronic integrated circuits can be thought of as the "brains" of a system and MEMS augments this decision-making capability with "eyes" and "arms", to allow microsystems to sense and control the environment. Sensors gather information from the environment through measuring mechanical, thermal, biological, chemical, optical, and magnetic phenomena. The electronics then process the information derived from the sensors and through some decision making capability direct the actuators to respond by moving, positioning, regulating, pumping, and filtering, thereby controlling the environment for some desired outcome or purpose. Because MEMS devices are manufactured using batch fabrication techniques similar to those used for integrated circuits, unprecedented levels of functionality, reliability, and sophistication can be placed on a small silicon chip at a relatively low cost.

"Microprocessor" is a processor on an integrated circuit (IC) chip. The processor may be one or more processor on one or more IC chip. The chip is typically a silicon chip with thousands of electronic components that serves as a central processing unit (CPU) of a computer or a computing device.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either $\alpha$-, $\beta$-, or $\omega$-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure.

A "nanomaterial" as used herein refers to a structure, a device or a system having a dimension at the atomic, molecular or macromolecular levels, in the length scale of approximately 1-100 nanometer range. Preferably, a nanomaterial has properties and functions because of the size and can be manipulated and controlled on the atomic level.

A "carbon nanotube" refers to a fullerene molecule having a cylindrical or toroidal shape. A "fullerene" refers to a form of carbon having a large molecule consisting of an empty cage of sixty or more carbon atoms.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers.

An "oligonucleotide" is a polynucleotide having 2-20 nucleotides. Analogs also include protected and/or modified monomers as are conventionally used in polynucleotide synthesis. As one of skill in the art is well aware, polynucleotide synthesis uses a variety of base-protected nucleoside derivatives in which one or more of the nitrogens of the purine and pyrimidine moiety are protected by groups such as dimethoxytrityl, benzyl, tert-butyl, isobutyl and the like.

For instance, structural groups are optionally added to the ribose or base of a nucleoside for incorporation into a polynucleotide, such as a methyl, propyl or allyl group at the 2'-O position on the ribose, or a fluoro group which substitutes for the 2'-O group, or a bromo group on the ribonucleoside base. 2'-O-methyloligoribonucleotides (2'-O-MeORNs) have a higher affinity for complementary polynucleotides (especially RNA) than their unmodified counterparts. Alternatively, deazapurines and deazapyrimidines in which one or more N atoms of the purine or pyrimidine heterocyclic ring are replaced by C atoms can also be used.

The phosphodiester linkage, or "sugar-phosphate backbone" of the polynucleotide can also be substituted or modified, for instance with methyl phosphonates, O-methyl phosphates or phosphororthioates. Another example of a polynucleotide comprising such modified linkages for purposes of this disclosure includes "peptide polynucleotides" in which a polyamide backbone is attached to polynucleotide bases, or modified polynucleotide bases. Peptide polynucleotides which comprise a polyamide backbone and the bases found in naturally occurring nucleotides are commercially available.

When the macromolecule of interest is a peptide, the amino acids can be any amino acids, including α, β, or Ω-amino acids. When the amino acids are α-amino acids, either the L-optical isomer or the D-optical isomer may be used. Additionally, unnatural amino acids, for example, β-alanine, phenylglycine and homoarginine are also contemplated by the embodiments of the invention. These amino acids are well-known in the art.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

The term "sequence" refers to the particular ordering of monomers within a macromolecule and it may be referred to herein as the sequence of the macromolecule.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies.

A "receptor" is molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term "receptors" is used herein, no difference in meaning is intended. A "Ligand Receptor Pair" is formed when two macromolecules have combined through molecular recognition to form a complex. Other examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value would be antibiotics against opportunistic fungi, protozoa, and those bacteria resistant to the antibiotics in current use.

b) Enzymes: For instance, one type of receptor is the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the-development of vaccines of which the immunogen is based on one or more of such sequences or lead to the development of related diagnostic agents or compounds useful in therapeutic treatments such as for auto-immune diseases (e.g., by blocking the binding of the "anti-self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant.

f) Hormone receptors: Examples of hormones receptors include, e.g., the receptors for insulin and growth hormone. Determination of the ligands which bind with high affinity to a receptor is useful in the development of, for example, an oral replacement of the daily injections which diabetics take to relieve the symptoms of diabetes. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

The phrase "SERS active particle" refers to a particle that produces the surface-enhanced Raman scattering effect. The SERS active particles reflect an incoming stimuli such as a laser. The analyte emission is the Raman signal. In response to laser stimuli, the molecule will emit a characteristic set of molecular vibrations, measured in wavenumber units ($cm^{-1}$). Certain parts of the molecule will experience greater perturbations and corresponding vibrations will be stronger, yielding a higher intensity peak. Generally, the most intense Raman signal intensity peak is measured/evaluated. This peak intensity is usually reported after correcting for the background signal. In SERS, the interaction of a high surface area material such as nanoparticles with the analyte of interest, increases the intensity of the observed Raman peaks. The result of this is that SERS signal can be detected at much lower concentrations than typical Raman, on the order of $10^4$-$10^{14}$. The Raman peaks are thus "surface-enhanced." The enhanced Raman scattering effect provides a greatly enhanced Raman signal from Raman-active analyte molecules that have been adsorbed onto certain specially-prepared SERS active particle surfaces. Typically, the SERS active particle surfaces are metal surfaces. Increases in the intensity of Raman signal have been regularly observed on the order of $10^4$-$10^{14}$ SERS enhancement of Raman signal for some systems. SERS active particles include a variety of metals including coinage (Au, Ag, Cu), alkalis (Li, Na, K), Al, Pd and Pt.

As used herein, "Raman-active organic compound" refers to an organic molecule that produces a unique SERS signature in response to excitation by a laser. A variety of Raman-active organic compounds are contemplated for use as components in COINs. In certain embodiments, Raman-active organic compounds are polycyclic aromatic or heteroaromatic compounds. Typically the Raman-active organic compound has a molecular weight less than about 300 Daltons.

Additional, non-limiting examples of Raman-active organic compounds useful in COINs include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluresceins, aminoacridine, and the like.

The term "complementary" refers to the topological compatibility or matching together of interacting surfaces of a ligand molecule and its receptor. Thus, the receptor and its ligand can be described as complementary, and furthermore, the contact surface characteristics are complementary to each other.

The term "waveguide" refers to a device that controls the propagation of an electromagnetic wave so that the wave is forced to follow a path defined by the physical structure of the guide. Generally speaking, the electric and magnetic fields of an electromagnetic wave have a number of possible arrangements when the wave is traveling through a waveguide. Each of these arrangements is known as a mode of propagation. Optical waveguides are used at optical frequencies. An "optical waveguide" is any structure having the ability to guide optical energy. Optical waveguides may be (a) thin-film deposits used in integrated optical circuits (IOCs) or (b) optical fibers.

The term "optical switch" refers to a switch that enables signals in optical fibers or integrated optical circuits (IOCs) to be selectively switched from one circuit to another. An optical switch may operate by (a) mechanical means, such as physically shifting an optical fiber to drive one or more alternative fibers, or (b) electro-optic effects, magneto-optic effects, or other methods. Slow optical switches, such as those using moving fibers, may be used for alternate routing of an optical transmission path. Fast optical switches, such as those using electro-optic or magneto-optic effects, may be used to perform logic operations. One type of an optical switch is a thin film optical switch, which is a switch having multilayered films of material of different optical characteristics, that is capable of switching transmitted light by using electro-optic, electro-acoustic, or magneto-optic effects to obtain signal switching, and is usually used as a component in integrated optical circuits. Thin-film optical switches may support only one propagation mode.

The term "PIN diode" refers to positive-intrinsic-negative diode. A photodiode with a large, neutrally doped intrinsic region sandwiched between p-doped and n-doped semiconducting regions. A PIN diode exhibits an increase in its electrical conductivity as a function of the intensity, wavelength, and modulation rate of the incident radiation. A PIN diode is also called photodiode.

The terms "spectrum" or "spectra" refer to the intensities of electromagnetic radiation as a function of wavelength or other equivalent units, such as wavenumber, frequency, and energy level.

The term "spectrometer" refers to an instrument equipped with scales for measuring wavelengths or indexes of refraction.

The term "dispersive spectrometer" refers to a spectrometer that generates spectra by optically dispersing the incoming radiation into its frequency or spectral components. Dispersive spectrometers can be further classified into two types: monochromators and spectrographs. A monochromator uses a single detector, narrow slit(s) (usually two, one at the entrance and another at the exit port), and a rotating dispersive element allowing the user to observe a selected range of wavelength. A spectrograph, on the other hand, uses an array of detector elements and a stationary dispersive element. In this case, the slit shown in the is removed, and spectral elements over a wide range of wavelengths are obtained at the same time, therefore providing faster measurements with a more expensive detection system.

The term "dispersive element" refers to a component of a dispersive spectrometer that can disperse electromagnetic radiation such as light. Dispersive elements include prisms and gratings.

The term "interferometer" refers to an instrument that uses the principle of interference of electromagnetic waves for purposes of measurement. For example, it could be any of several optical, acoustic, or radio frequency instruments that use interference phenomena between a reference wave and an experimental wave or between two parts of an experimental wave to determine wavelengths and wave velocities, measure very small distances and thicknesses, and calculate indices of refraction.

The term "non-dispersive element" refers to an interferometer that does not disperse electromagnetic radiation in spatial domain but instead creates a phase shift in the electromagnetic radiation.

The term "Fourier transform spectrometer" refers to a spectrometer used for Fourier transform spectroscopy, which is a measurement technique whereby spectra are collected based on the response from a pulse of electromagnetic radiation. It can be applied to variety of types of spectroscopy including infrared spectroscopy (FTIR), nuclear magnetic resonance, and electron spin resonance spectroscopy. Fourier transform spectroscopy can be more sensitive and has a much shorter sampling time than conventional spectroscopic techniques. For example, in a conventional (or "continuous wave") nucleic magnetic resonance spectrometer, a sample is exposed to electromagnetic radiation and the response (usually the intensity of transmitted radiation) is monitored. The energy of the radiation is varied over the desired range and the response is plotted as a function of radiation energy (or frequency). At certain resonant frequencies characteristic of the specific sample, the radiation will be absorbed resulting in a series of peaks in the spectrum, which can then be used to identify the sample. (In magnetic spectroscopy, the magnetic field is often varied instead of the frequency of the incident radiation, though the spectra are effectively the same as if the field had been kept constant and the frequency varied. This is largely a question of experimental convenience. Instead of varying the energy of the electromagnetic radiation, Fourier Transform nucleic magnetic resonance spectroscopy exposes the sample to a single pulse of radiation and measures the response. The resulting signal, called a free induction decay, contains a rapidly decaying composite of all possible frequencies. Due to resonance by the sample, resonant frequencies will be dominant in the signal and by performing a mathematical operation called a Fourier transform on the signal the frequency response can be calculated. In this way the Fourier transform nucleic magnetic resonance spectrometer can produce the same kind of spectrum as a conventional spectrometer, but generally in a much shorter time.

The term "optical bench" refers to an apparatus for observation and measurement of optical phenomena. For example, it could be an apparatus such as a special table or rigid beam, for the precise positioning of light sources, screens, and optical instruments used for optical and photometric studies, having a ruled bar to which these devices can be attached and along which they can be readily adjusted.

The term "interferogram" or "Fourier transform spectrum" used herein means the detector response as a function of the optical path length difference caused by the interference of electromagnetic radiation.

The term "container" means an area or vessel that holds a sample, such as a solid or solution, of interest. The term is synonymous with the term "well," such as for example, a sample plate containing one or more sample wells. Sample plate refers to an apparatus in which, or on which, a sample or specimen can be placed for evaluation or observation. For example, a sample plate may have 1 or more sample containers (wells) wherein one or more samples of interest are placed for laboratory experiments and/or observation and analysis. A container (i.e., well) can hold very large or very minute sample sizes or volumes. For example, a large sample container could hold 500 mL or more of sample; a small container can hold 1 nanoliter (nl) of sample or less. Various sample plate and container capacities are entirely dependent on a user's needs and selection, and are well known in the art. Embodiments of this invention are not limited to sample plate size, material of construction, shape, density, or weight. Similarly, containers (wells) can be variable size depending on user needs, and can be variable depths, capacities, shapes, or symmetries. If a sample plate has more than one container (well), each container can be filled with a different sample for evaluation. Sample containers within a single sample plate can be of variable capacities and shapes.

The term "optical reflective surface" refers to a surface that reflects part or all of the light impinged upon it, including all known light wavelengths (visible and invisible). Optical reflective surface is a broad term used to describe any material or surface that can reflect back the incoming light or laser. An "optical reflective material" is a material that, when applied or coated onto a surface (or present behind a transparent surface), will create an optical reflective surface.

The term "coating" refers to a substance applied to a surface. For example, a sample plate, and/or a sample container, can be coated with a substance to provide for an optical reflective surface, or to enhance the optical reflectivity of a surface. A coating may be on the top or bottom surface of an object, depending on one's perspective.

The term "Raman signal intensity" refers to the signal intensity caused by Raman interactions. In response to laser stimuli, certain molecules will emit a characteristic set of molecular vibrations, measured in wavenumber units ($cm^{-1}$). Certain parts of the molecule will experience greater perturbations and corresponding vibrations will be stronger, yielding a higher intensity peak. Generally, the most intense peak is measured as the Raman signal intensity. Peak Raman intensity is usually reported after correcting for the background signal.

Raman excitation and signal detection occurs after probing a sample at a chosen light wavelength (i.e., impinging light of a certain wavelength or wavelengths), such as for example 785 nm, 514 nm, 532 nm. Embodiments of the invention need not be limited to these wavelengths if different lasers provide excitation in a given sample.

The term "excitation light intensity" refers to the intensity of a light source that is applied to a sample. For example, the energy of an incoming laser beam or light beam used to perturb or excite the sample is the excitation signal intensity. Common excitation light wavelengths used to induce for Raman excitation are 785 nm, 532 nm, and 514 nm. However, embodiments of this invention are not limited to these wavelengths.

The term "enhance" or "enhancement" refers to the increase or improvement of signal intensity and/or detection. In standard, unimproved sample plates and containers, light is impinged on the plate and a certain amount of the light is reflected and detected or observed. This is the baseline performance (reflectivity) of a sample plate or container. In embodiments of the invention, the sample plate and/or containers are coated with a optical reflective material that improves reflectivity of excitation light intensity and Raman signal intensity. Accordingly, the amount of light that is detected is improved (or enhanced, optimized), because the sample plate/container exhibits reflectivity. Enhancement refers to any improvement of total signal intensity compared to (relative to) non-coated sample plates or containers.

Embodiments of this invention relate to sample plates that have sample containers, or wells, the surface of which is partially or totally coated with an optical reflective material that optimizes Raman signal detection. Other embodiments include methods of enhancing the Raman signal and excitation light by using sample plates having containers (wells) that are coated with a reflective substance, and systems that incorporate sample plates having sample containers that are at least partially coated with an optical reflective material.

One embodiment of this invention is a surface-enhanced sample plate that enhances light signal reflectivity an includes one or more sample containers (wells) to hold test samples, and an optical reflective surface coating on at least part of the sample container that enhances the total light signal reflectivity of the sample plate relative to an uncoated sample plate container. Light from an excitation light source impinges on a sample within a coated sample container, causing Raman scattering. The optical reflective material enhances Raman scattering, and also enhances the excitation signal reflectivity. These signals are reflected back to the optics in an improved (enhanced) manner, thereby improving signal for detection by the optics or sensors.

Preferably, the sample plate has one container (well). More preferably, the sample plate has a plurality (i.e., more than 1) container (well). In this manner, a sample plate can be used with multiple aliquots of the same sample, or alternatively, with multiple different samples. Certain embodiments include high-throughput devices wherein multiple samples can be analyzed.

Preferably, the sample plate is made of a material selected from the group consisting of glass, metal, plastic, polystyrene, and polymer. It is envisioned that the sample plate material can be coated with one or more optical reflective materials, described below.

Preferably, the optical reflective material includes metals selected from the group consisting of gold, silver, aluminum, and combinations thereof. Preferably, the optical reflective material is applied to the surface of a sample plate container, or portions thereof. The type and thickness of optical reflective material on the sample plate container (well) can be optimized according to preferred excitation light wavelength and/or user needs or preferences.

The optical reflective material is selected based on a desired light excitation wavelength. The excitation light, which is the light signal emitted from the light source such as a laser, includes light wavelengths from either the visible or invisible spectrum. Excitation light emitted from the light source has an excitation light intensity value, depending on the intensity of the light source.

The optical reflective material enhances excitation light intensity by improving reflectivity of the sample container. Alternatively, the optical reflective material enhances Raman signal intensity. Preferably, the optical surface coating enhances both excitation light intensity and Raman signal intensity.

The intensity of the proposed signal enhancement is a function of the reflectivity of light from the sample plate. If the sample plate is not made of reflective material, the top layer of a non-reflective plate can be coated with, or made of, optical reflective materials that include a reflective metal (e.g., aluminum, steel, gold, silver). The preferable metal included in the optical reflective material when green laser excitation wavelengths, such as 514 nm or 532 nm are used, is aluminum. Preferably, optical reflective materials containing gold or silver metal are used on sample containers for red or infrared wavelength laser excitation, such as 785 nm.

Alternatively, the top surface or coating of a sample plate/container can be transparent, and the layer below the transparent surface can be a reflective metal or engineered mirror layer or selective filter.

Preferably, the total light signal enhancement (T), provided by embodiments of the invention, is increased by a factor of about 1-4, wherein T is given by the equation $T=(1+R)^2$ where R is the light surface reflectivity "enhancement factor" of the coated sample plate. It is envisioned that total light signal enhancement can range from T=about 0.20 to about 4. As stated above, the enhancement observed in embodiments of the invention is relative to the total light signal detected in sample containers without an optical reflective material coating.

In a typical, non-optimized sample container Raman signal is represented as $Signal_{Raman}$ in response to an incoming laser of a given power, $P_{Laser}$.

In an optimized sample container, where the incident laser signal is reflected off an optical reflective material on the container walls, $Power_{Raman}$ of the laser results within the sample container that is a combination of the incoming laser signal intensity and the laser signal intensity that reflects off the well surface. In other words, $$Power_{Raman} = P_{Laser} + RP_{Laser} = P_{Laser}(1+R).$$

However, the signal intensity that is detected will be a function of how well the laser produces the desired Raman signal. This factor is expressed as a, where $Signal_{Raman} = \alpha * Power_{Raman}$. This is the laser intensity that results in detected Raman (or SERS) signal.

In addition to the laser signal reflecting off of the container, a portion of the signal from within the sample will also emit towards the container walls and reflect back to the collection (focal) area.

Thus, the $Power_{Total}$ exhibited by the sample is a combination of the laser signal intensity and the detected signal intensity, both of which reflect from the optimized container surface and result in enhanced original signal, as in:

$$\begin{aligned} Signal_{Total} &= (\alpha * Power_{Raman}) + (\alpha * R * Power_{Raman}) \\ &= \alpha * Power_{Raman}(1+R) \\ &= \alpha * P_{Laser}(1+R)*(1+R) \\ &= \alpha * P_{Laser}(1+R)^2 \end{aligned}$$

Thus, the enhancement factor provided in embodiments of this invention is equal to $(1+R)^2$. For example, where the optical reflective material has an R of 0.80, the enhancement factor is $(1+0.8)^2$ which equals 3.24x.

In preferred embodiments, the optical reflective material covers or coats the entire surface of the sample container (well). In other embodiments, the optical reflective material is present on less than 100% of the surface of the sample container, i.e., the entire container (well) is not coated. For example, the lower ⅓ or ⅔ of the well can be covered with the optical reflective material.

Sample container wells include any shape that is conducive to holding samples. Exemplary sample container shapes include round-bottom, square-bottom, and conical bottom. Preferably, the lower aspect of the sample containers are spherical, and have a capacity (volume) represented by the following equation:

$$\frac{1}{2}\left(\frac{4}{3}\pi r^3\right) + \Delta\pi r^2 = V \qquad (I)$$

where the first term describes the volume of a hemisphere, which is ½ the volume of a complete sphere (where r in the first term is the radius of a sphere). The second term is from the volume of a cylinder, which is a rough approximation of the volume of the water based solution since the top of a water droplet in a conventional well is actually rounded.

In certain embodiments, the optical reflective material is located underneath the surface of a transparent or essentially transparent sample container. That is to say, the optical reflective surface can be either on the surface of the sample container, or alternatively, below the surface of a transparent sample container.

In certain embodiments, the optical reflective material is coated or protected in order to be resistant to degradation. Common optical coatings for aluminum or gold include silicon oxide, silicon dioxide, also known as silica.

Another embodiment of the invention is a method of enhancing the Raman signal and excitation light including the steps of obtaining a sample plate having one or more sample containers, coating at least a portion of a sample container with an optical reflective material, exposing the coated sample container (which holds a sample of interest) to an excitation light source such as a laser; and detecting the light signal emanating (reflecting) from the sample container.

The sample plate may have one sample container (well), or a plurality of sample containers (wells).

Preferably, the sample plate is made of a material selected from the group consisting of glass, metal, plastic, polystyrene, and polymer. Alternatively, the top layer or coating of a sample plate or container can be transparent (e.g., glass, quartz), and the layer below the transparent layer can be a reflective metal or engineered mirror layer.

Preferably, the sample container, or a portion thereof, is coated with an optical reflective material that includes metals selected from the group consisting of gold, silver, aluminum, and combinations thereof.

The method includes the detection of Raman signal intensity. Alternatively, the method includes the detection of excitation light intensity. Preferably, the method includes the detection of both Raman signal intensity and excitation light intensity.

Another embodiment of the invention is a system including a sample pate having one or more sample containers that are at least partially coated with an optical reflective material, a sample to be evaluated, an excitation light source such as a laser, and a detection device capable of detecting reflected excitation and Raman light signal that emanates and or reflects from the sample plate or sample container.

Preferably, the sample plate is made of a material selected from the group consisting of glass, metal, plastic, polystyrene, polymer, or combinations thereof. Alternatively, the top surface or coating of a sample plate or container can be transparent (e.g., glass, quartz), and the surface below the overlying transparent surface is a reflective metal coating or engineered mirror layer.

Preferably, the detection device includes a fluorescence detector, a spectrophotometer, a Raman spectrophotometer, a magnetic detector, a magnetic tunnel junction sensor, a proximity scintillation surface, a luminometer, a scintillation counter, a charge coupled device camera, or a gamma counter.

Preferably, the detection device includes a photodiode, an avalanche photodiode, or a photo-multiplier tube. Certain embodiments of the system include a detection device with at least one optical filter.

Preferably, the system includes a container, a reservoir, or a fluidic channel for collecting a liquid comprising the sample after the sample is removed from a sample plate container.

Preferably, the optical reflective material includes metals selected from the group consisting of gold, silver, aluminum, and combinations thereof.

Figure 1:
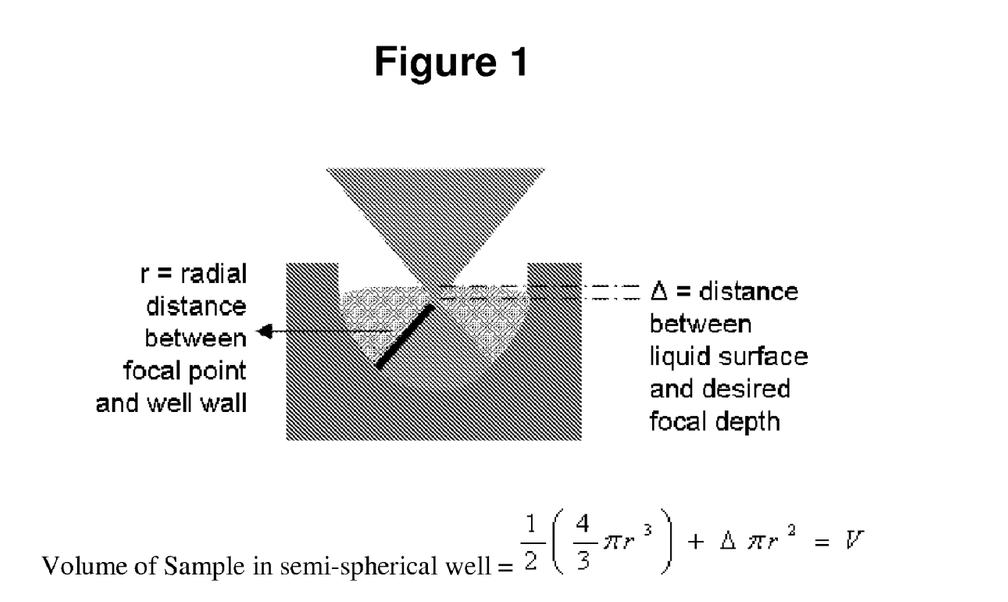
FIG. 1 shows the key focal point parameters, $\Delta$ and $r$, in a sample container (well) and the equation for calculating the volume of a semi-spherical sample container.

FIG. 1 illustrates the key parameters, $\Delta$ and r, in a sample container (well) where $\Delta$ is the distance between a liquid sample surface and a desired focal depth, and r is the radial distance between the focal point and a container (well) wall. In a typical solution-based Raman experiment setup, shown in FIG. 1, the excitation laser beam is focused at a point some distance below the solution surface, distance A. Beyond the focal point the laser beam becomes more diffuse, eventually reaching the walls of the sample container. The radial distance between the focal point and the wall is defined as "r." In the typical, non-optimized experiment the laser excitation is focused from the top of the sample, and the sample Raman signal is collected from the top, as illustrated in FIG. 2.

Figure 2:
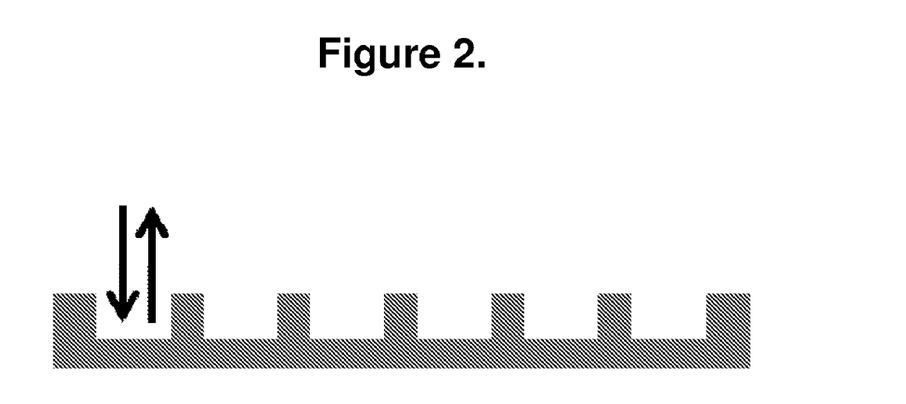
FIG. 2 shows typical laser excitation and signal detection, such as in a plastic, non-reflective (non-optimized) sample plate with uncoated sample containers.

FIG. 2 is an illustration of typical laser excitation and signal detection of signal from a sample container (well), such as for example, from a plastic, non-reflective sample container.

Figure 3:
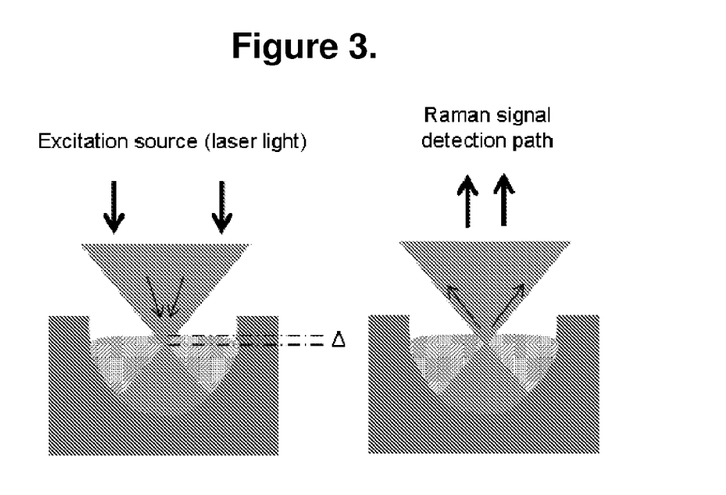
FIG. 3 shows a surface-enhanced reflective (optimized) plate enhancing laser excitation intensity.

In an embodiment wherein the sample plate and/or sample containers are reflective, or coated with an optical reflective material, the laser beam excitation signal is enhanced, perhaps doubled, as illustrated in FIG. 3. Sample plates of the invention that have reflective properties that enhance the excitation signal and Raman signal, relative to an uncoated sample plate, can be made of various materials, for example, glass, polystyrene, or plastic coated with and optical reflective material or materials (such as for example, gold, silver or aluminum) that are compatible with the excitation laser being used. These metal optical reflective materials that coat the sample plates and/or containers (wells) can be functionalized or coated to be chemically resistant. Such techniques are well known in the art, and include for example, silicon oxide and silicon dioxide (or silica) coatings.

The signal enhancement afforded by the products and methods of the invention occur as the reflective optical material enhances the excitation signal intensity and/or the Raman signal intensity. If one or both of these signal intensities is enhanced, a greater total signal is available for detection by an optical signal detector, such as for example, a microscope or scanner that is capable of detecting the reflected light, or others as outlined above. This is demonstrated in FIG. 4.

Figure 4:
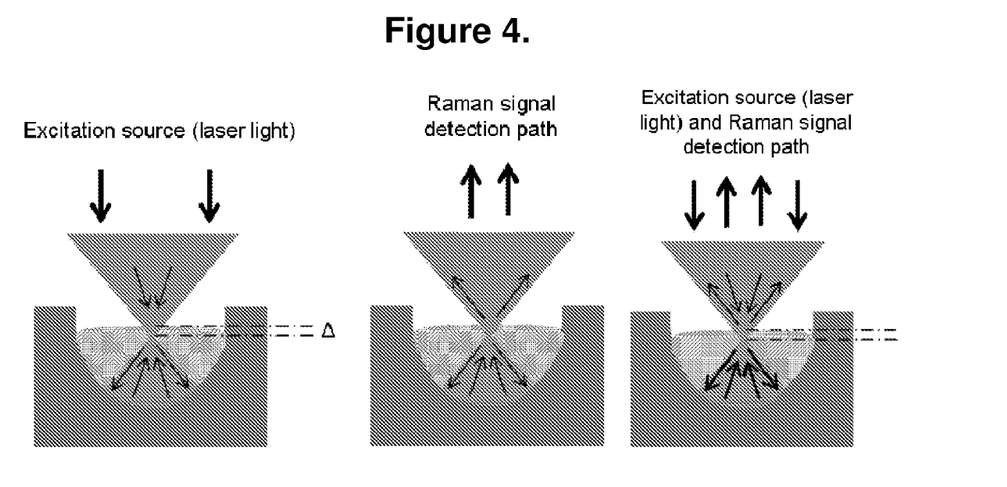
FIG. 4 shows a surface-enhanced reflective (optimized) plate enhancing laser excitation intensity and Raman signal intensity.

FIG. 4. illustrates a sample container or sample analysis plate having wells (containers) with a reflective surface, such as for example, sample plates or containers (wells) that are coated with an optical reflective material. Such a reflective surface reflects back a greater amount of the laser excitation signal, nearly doubling (1.9x) the laser intensity at the focal point. The surface coated with an optical reflective material also reflects back the resulting Raman signals created in the sample, so that the detected signal is nearly doubled (1.9x) as well. Optimally, the total signal enhancement could be as much as 3.8x or more of the original signal intensity, based on Raman signal enhancement (1.9x)+excitation signal enhancement (1.9x). However, total signal enhancement of 2-3x would be desirable as well, or even, any total signal enhancement greater than 1x.

Embodiments of the invention include methods of improving focusing algorithms. Specifically, sample plates and/or containers with reflective characteristics, such as coatings with optical reflective materials, improve Raman signal intensity originating from the sample, as described above. Because of the relationship of Raman signal and narrow focal point position in non-optimized sample containers, polynomial fit is not very accurate. Adapting a sample plate with sample containers (wells) having optical reflective characteristics, the Raman signal intensity will be enhanced as the correct focus point is approached.

Figure 5:
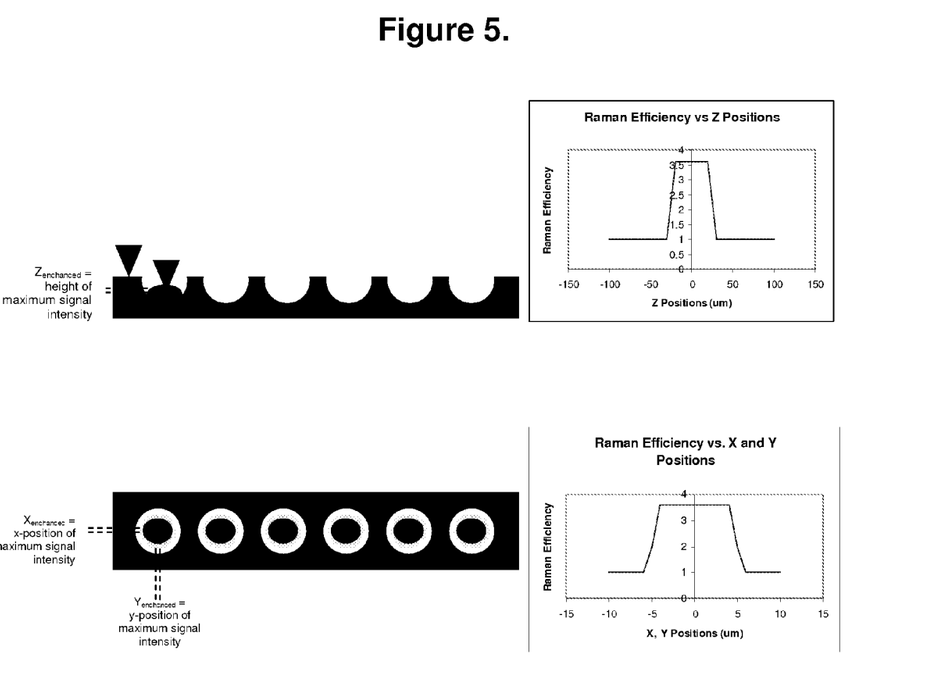
FIG. 5 shows how the detected signal (as measured by Raman peak intensity) would vary with adjustments in z and x/y position in the optimized well. An algorithm to maximize the detected peak intensity could be used in either a manual focusing method or auto focusing algorithm.
Figure 6:
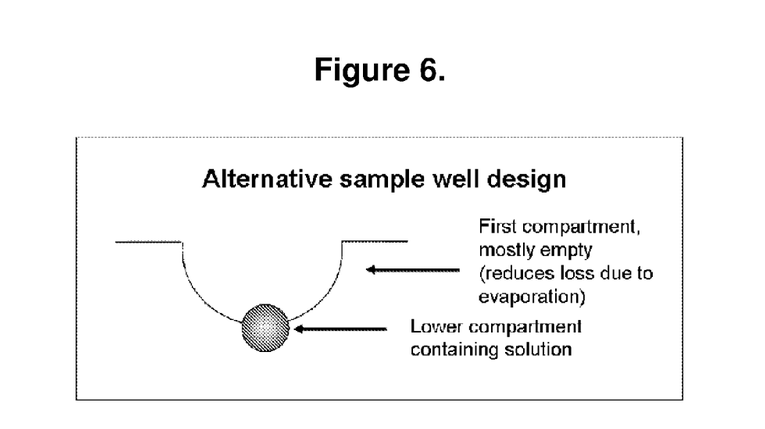
FIG. 6 shows an alternative optimize sample container design wherein only the lower aspect of the well is coated with the optical reflective material.

In each sample container, there is only one point where maximum focus and maximum signal intensity occur; this is the desirable focal point. Focusing in the z-direction is relatively sensitive to position. Using the methods described herein, it is possible to plot intensity vs. z-height and obtain a maximum signal intensity value ("sweet spot") for the z-position (FIG. 5). In non-optimized sample containers, this is impossible in the x/y directions because there is no "sweet spot" for the x-y position. Here, with laser power and signal reflecting back to a specific x-y-z point, the z spot can be identified thereby pinpointing the optimal focal point within the sample container.

EXAMPLE 1

A plastic sample plate is obtained that contains 96 individual sample wells (containers). The plate holds Raman-active samples of interest, wherein samples are placed in one or more of the sample containers. The sample wells have a round-bottom shape such that each well holds a sample volume that can be calculated based on the volume of a half-sphere and of a cylinder, according to the equation:

$$\frac{1}{2}\left(\frac{4}{3}\pi r^3\right) + \Delta \pi r^2 = V$$

The samples are analyzed by impinging a green-wavelength laser light source onto the sample, causing light to enter the sample causing Raman excitation. The excitation light intensity (from the laser source) and the Raman signal intensity are enhanced by an optically reflective material on the surface of the sample containers. Because green laser excitation wavelengths, such as 514 nm or 532 nm, are used, the optical reflective material coating contains aluminum. The presence of the optical reflective material enhances the amount of excitation light and Raman excitation light signal that are reflected back from the sample container to a detection device.

The optical reflective material has a reflectivity factor ("R") factor of 0.80. Therefore, the total enhancement of the coated sample plates due to increased reflectivity of excitation and Raman light is $(1+0.8)^2$ which is 3.24x.

EXAMPLE 2

An optically transparent sample plate is obtained that contains 96 individual sample wells (containers). The plate is used to hold Raman-active samples of interest, wherein samples are placed in one or more of the sample containers. The sample wells have a round-bottom shape such that they hold a sample volume that can be calculated based on the volume of a half-sphere and of a cylinder, according to the equation:

$$\frac{1}{2}\left(\frac{4}{3}\pi r^3\right) + \Delta \pi r^2 = V$$

The samples are analyzed by impinging a green-wavelength laser light source onto the sample, causing light to enter the sample causing Raman excitation. The excitation light intensity (from the laser source) and the Raman signal intensity are enhanced by an optically reflective material located below the sample containers. Specifically, the transparent sample plate is placed into a "cassette" which is underneath the transparent sample plate. The cassette is constructed of a material that is optically reflective. Because green laser excitation wavelengths, such as 514 nm or 532 nm, are used, the optical reflective cassette underneath the transparent sample plate/containers contains aluminum. The presence of the optical reflective material below the sample containers enhances the amount of excitation light and Raman excitation light signal that are reflected back from the sample container to a detection device.

The optical reflective material has a reflectivity factor ("R") factor of 0.95. Therefore, the total enhancement of the coated sample plates due to increased reflectivity of excitation and Raman light is $(1+0.95)^2$ which is 3.80x.

EXAMPLE 3

A plastic sample plate is obtained that contains 96 individual sample wells (containers). The plate is used to hold Raman-active samples of interest, wherein samples are placed in one or more of the sample containers. The sample wells have a round-bottom shape such that they hold a sample volume that can be calculated based on the volume of a half-sphere and of a cylinder, according to the equation:

$$\frac{1}{2}\left(\frac{4}{3}\pi r^3\right) + \Delta \pi r^2 = V$$

The samples are analyzed by impinging a green-wavelength laser light source onto the sample, causing light to enter the sample causing Raman excitation. The excitation light intensity (from the laser source) and the Raman signal intensity are enhanced by an optically reflective material on the surface of the sample containers. Because a red laser excitation wavelength, such as 785 nm, is used, the optical reflective material coating contains gold or silver. The presence of the optical reflective material enhances the amount of excitation light and Raman excitation light signal that are reflected back from the sample container to a detection device.

The optical reflective material has a reflectivity factor ("R") factor of 0.90. Therefore, the total enhancement of the coated sample plates due to increased reflectivity of excitation and Raman light is $(1+0.9)^2$ which is 3.61x.

Commercial applications for the products and methods described herein include environmental toxicology and remediation, biomedicine, materials quality control, food and agricultural products monitoring, anesthetic detection, automobile oil or radiator fluid monitoring, breath alcohol analyzers, hazardous spill identification, explosives detection, fugitive emission identification, medical diagnostics, fish freshness, detection and classification of bacteria and microorganisms both in vitro and in vivo for biomedical uses and medical diagnostic uses, monitoring heavy industrial manufacturing, ambient air monitoring, worker protection, emissions control, product quality testing, leak detection and identification, oil/gas petrochemical applications, combustible gas detection, H₂S monitoring, hazardous leak detection and identification, emergency response and law enforcement applications, illegal substance detection and identification, arson investigation, enclosed space surveying, utility and power applications, emissions monitoring, transformer fault detection, food/beverage/agriculture applications, freshness detection, fruit ripening control, fermentation process monitoring and control applications, flavor composition and identification, product quality and identification, refrigerant and fumigant detection, cosmetic/perfume/fragrance formulation, product quality testing, personal identification, chemical/plastics/pharmaceutical applications, leak detection, solvent recovery effectiveness, perimeter monitoring, product quality testing, hazardous waste site applications, fugitive emission detection and identification, leak detection and identification, perimeter monitoring, transportation, hazardous spill monitoring, refueling operations, shipping container inspection, diesel/gasoline/aviation fuel identification, building/residential natural gas detection, formaldehyde detection, smoke detection, fire detection, automatic ventilation control applications (cooking, smoking, etc.), air intake monitoring, hospital/medical anesthesia & sterilization gas detection, infectious disease detection and breath applications, body fluids analysis, pharmaceutical applications, drug discovery, tele-surgery, and the like.

This application discloses several numerical range limitations that support any range within the disclosed numerical ranges even though a precise range limitation is not stated verbatim in the specification because the embodiments of the invention could be practiced throughout the disclosed numerical ranges.

Embodiments and examples disclosed herein are exemplary and not intended to be limiting in nature. Finally, the entire disclosure of the patents and publications referred in this application, if any, are incorporated herein in entirety by reference.

The invention claimed is:

1. A sample plate comprising:
   one or more sample containers for holding test samples; and
   a visible spectrum optical reflective material coating at least a part of the sample container,
   wherein the visible spectrum optical reflective material enhances visible light signal reflectivity in relative to a sample plate without the visible spectrum optical reflective material coating,
   wherein the one or more sample containers for holding test samples are configured to hold a liquid, and wherein bottoms of the one or more sample containers have a rounded surface having a single point of maximum focus.

2. The sample plate of claim 1, wherein the sample plate is comprised of a material selected from a group consisting of glass, metal, plastic, polystyrene, and polymer.

3. The sample plate of claim 1 wherein the sample container is constructed of a transparent material placed over the visible spectrum optical reflective material.

4. The sample plate of claim 1, wherein the visible spectrum optical reflective material comprises metals selected from a group consisting of gold, silver, aluminum, and combinations thereof.

5. The sample plate of claim 4, wherein the visible spectrum optical reflective material is selected based on a desired visible light excitation wavelength.

6. The sample plate of claim 4, wherein the visible spectrum optical reflective material enhances excitation light intensity.

7. The sample plate of claim 4, wherein the visible spectrum optical reflective material enhances Raman signal intensity.

8. The sample plate of claim 1, wherein total light signal enhancement (T) is increased by a factor of about 1-4.

9. The sample plate of claim 8 wherein T is given by:

$$T(1+R)^2$$

where R is a surface reflectivity enhancement factor.

10. The sample plate of claim 1, wherein the visible spectrum optical reflective material is present on an entire surface of the sample container.

11. The sample plate of claim 1, wherein the visible spectrum optical reflective material is present on less than 100% of an entire surface of the sample container.

12. The sample plate of claim 1, wherein the visible spectrum optical reflective material is functionalized to be chemically resistant to degradation.

13. A method of enhancing Raman signal and excitation light comprising:
   obtaining a sample plate having one or more sample containers, wherein the bottoms of the one or more sample containers have a rounded surface having a single point of maximum focus;
   coating a portion of the sample container with a visible spectrum optical reflective material;
   exposing the sample container to excitation light of a desired wavelength, the excitation light causing Raman scattering; and
   detecting a light signal emanating from the sample container.

14. The method of claim 13 wherein the sample plate comprises 1 sample container.

15. The method of claim 13 wherein the sample plate comprises more than 1 sample container.

16. The method of claim 13, wherein the sample plate is comprised of a material selected from a group consisting of glass, metal, plastic, polystyrene, and polymer.

17. The method of claim 13 wherein the visible spectrum optical reflective material comprises a metals selected from a group consisting of gold, silver, aluminum, and combinations thereof.

18. The method of claim 13 wherein the visible spectrum optical reflective material is selected based on a desired light excitation wavelength.

19. The method of claim 13, further comprising detecting Raman signal intensity.

20. The method of claim 13, further comprising detecting excitation signal intensity.

21. A system comprising:
   a sample plate having one or more sample containers, wherein the at least a portion of the sample container includes a coating of a visible spectrum optical reflective material, wherein the visible spectrum optical reflective material comprises a metals selected from the group consisting of gold, silver, aluminum, and combinations thereof, and wherein bottoms of the one or more sample containers have a rounded surface having a single point of maximum focus;
   a sample to be evaluated;
   an excitation light source; and
   a detection device capable of detecting reflected excitation and Raman light signal.

22. The system of claim 21, wherein the sample plate comprises glass, metal, plastic, polystyrene, polymer, or a combination thereof.

23. The system of claim 21, wherein the detection device comprises a fluorescence detector, a spectrophotometer, a Raman spectrophotometer, a magnetic detector, a magnetic tunnel junction sensor, a proximity scintillation surface, a lurninometer, a scintillation counter, a charge coupled device camera or a gamma counter.

24. The system of claim 21, further comprising a container, a reservoir, or a fluidic channel for collecting a liquid comprising the sample after the sample is removed from the sample plate container.

25. The system of claim 21, wherein the detection device comprises a photodiode, an avalanche photodiode, or a photomultiplier tube.

26. The system of claim 21, wherein the detection device comprises an optical filter.

27. The system of claim 26, wherein the detection device comprises a multi-channel detector, a photodiode array, or a charge-coupled device (CCD).

28. The system of claim 27, wherein the detection device comprises a diffraction grating.

29. The sample plate of claim 1, wherein the visible spectrum optical reflective material has a thickness optimized to reflect light of wavelengths of about 514 nm, about 532 nm, or about 785 nm.

30. The method of claim 13, wherein the desired wavelength is selected from 514 nm, 532 nm, or 785 nm.

31. The method of claim 13, further comprising determining the point of maximum focus and/or maximum signal intensity.

32. The method of claim 31, further comprising plotting signal intensity of the light signal emanating from the sample container versus z-height in the sample container.

33. The method of claim 31, further comprising plotting signal intensity of the light signal emanating from the sample container versus x and/or Y position in the sample container.

34. The system of claim 21, wherein the excitation light source provides light at an excitation wavelength selected from 514 nm, 532 nm, or 785 nm.

35. The method of claim 13, wherein the one or more sample container for holding test samples are configured to hold a liquid.

36. The system of claim 21, wherein the one or more sample container for holding test samples are configured to hold a liquid.

* * * * *